US00PP16652P3

(12) United States Plant Patent
Tate

(10) Patent No.: US PP16,652 P3
(45) Date of Patent: Jun. 13, 2006

(54) RED MAPLE TREE NAMED 'RT4'

(50) Latin Name: *Acer Rubrum*
Varietal Denomination: RT4

(76) Inventor: Ray Tate, 435 Ray's Church Rd., Bishop, GA (US) 30621

( * ) Notice: Subject to any disclaimer, the term of this patent is extended or adjusted under 35 U.S.C. 154(b) by 74 days.

(21) Appl. No.: 10/964,318

(22) Filed: Oct. 13, 2004

(65) Prior Publication Data

US 2006/0090232 P1 Apr. 27, 2006

(51) Int. Cl.
*A01H 5/00* (2006.01)

(52) U.S. Cl. ..... Plt./224
(58) Field of Classification Search ..... Plt./224
See application file for complete search history.

(56) References Cited

PUBLICATIONS

"*Acer rubrum* 'Somerset' and 'Sun Valley'" by U.S. National Arboretum Plant Intro.*
"*Acer rubrum* 'October Glory' Red Maple" by Edward Gilman and Dennis Watson.*
"*Acer rubrum* 'Red Sunset' Red Maple" by Edward Gilman and Dennis Watson.*
"*Acer rubrum* 'Bradywine'" by U.S. National Arboretum Plant Intro.*
"*Acer rubrum* 'Bowhall' Red Maple" by Edward Gilman and Dennis Watson.*

* cited by examiner

*Primary Examiner*—Anne Marie Grunberg
*Assistant Examiner*—Annette H Para
(74) *Attorney, Agent, or Firm*—Polster, Lieder, Woodruff & Lucchesi, L.C.

(57) ABSTRACT

A Red Maple tree named 'RT4' and distinguished by having a bark of a striking reddish-brown color and capable of being reliably reproduced from vegetative cuttings.

4 Drawing Sheets

Latin name of the genus and species of the plant claimed: *Acer Rubrum.*

Variety denomination: 'RT4'.

BACKGROUND OF THE INVENTION

The present invention relates to a new and distinct variety of a Red Maple tree (*Acer rebrum*) to which I have given the varietal name 'RT4'.

DISCOVERY

I discovered my new variety of Red Maple tree in the Spring, 2002, growing in a production area of a commercial nursery in Morgan County, Ga. The tree was growing among a group of cultivated Red Maple trees which were grown from bare-root liners purchased from an Oregon nursery for liners in February, 2000, and planted in the Morgan County, Ga. nursery subsequent to that date. I therefore assume that my Red Maple tree is approximately 4 years old. The liners were purchased as October Glory® Red Maple trees that were asexually reproduced from tissue culture. Due to the nature of tissue culture, genetic variation is common, and I believe my Red Maple tree 'RT4' represents a mutation which occurred during the tissue culture process; or which is the result of tissue collected from a branch sport. All of the other trees in the group of Red Maple trees appear to be true October Glory Red Maple trees and exhibit none of the characteristics of my Red Maple tree 'RT4'.

Propagation

After observing my new tree for two years, 'RT4' was asexually propagated, using vegetative cuttings, at my direction in the Summer, 2004. This took place at my nursery in Bishop, Ga. No attempt was made to propagate 'RT4' prior to this time, nor were any trees in the block of trees where 'RT4' is located used for propagation purposes prior to this time. This propagation and its resulting progeny have proven that my new variety has characteristics which are firmly fixed. Further, these observations have confirmed my new variety represents a new and improved variety of Red Maple tree, as particularly evidenced by the striking reddish-brown bark of the tree and which can be reliably propagated asexually.

Uniqueness

'RT4' was observed to have a reddish-brown bark which is striking in color. This characteristic distinguishes my new tree from other typical seedlings of Red Maple trees and known cultivars.

Use

'RT4' has been observed for a period of time and is believed to be particularly useful wherever Red Maple are used; as a speciman tree in a lawn or park, besides streets, and in residential, city, and commercial plantings. Red Maple trees are considered a highly ornamental, very attractive tree, and my improved variety with its striking reddish-brown bark adds to its desirability in landscape setting.

SUMMARY OF THE INVENTION

Background

Red Maple trees are native to province of Newfoundland, Canada, south to Flordia, west to Minnesota, and southwest to Oklahoma and Texas in the United States. The trees prefer low, wet areas with acid soils, but are also found in drier soils at higher elevations; although growth in these latter areas is not vigorous. A Red Maple tree is typically pyramidal or elliptical when young, becoming ovoid or rounded as it matures. Seedling material is available over the natural range of the tree with respect to growth rate, leaf size and shape, and growth habit. However, the color of the bark is gray on all known seedlings and cultivars. My new cultivar differs significantly from the species in that its bark is a striking reddish-brown color. 'RT4' differs from October Glory in the color of its bark.

Industry Respresentation

Cultivated Red Maple is represented in the Industry both as seedling material and as cultivars. The most popular cultivars are October Glory® and Red Sunset®. Other popular cultivars include Autumn Flame®, 'Bowhall', and Summer Red®. In addition, the US National Arboretum has recently introuduced three (3) new cultivars: 'Brandywine', 'Somerset', and 'Sun Valley'. All of these cultivars have been selected for heat tolerance, fall color, or resistance to leafhopper damage which is a common problem among Red Maples.

Dr. Michael A. Dirr has listed fifty-eight (58) selections or cultivars of Red Maple, but none of these has the striking reddish-brown bark of my new tree. My new Red Maple tree is currently three inches (3") in caliper, eighteen feet (18') tall, and has a six foot (6') wide canopy. These dimensions are similar to those of the other maples planted in the block where my Red Maple tree is found and correspond to those dimensions expected for a cultivar and most seedling maples of this age.

DESCRIPTION OF THE DRAWINGS (PHOTOGRAPHS)

The accompanying photographs depict the color of the tree and the foliage of my new variety as nearly as is reasonably possible to make the same in a color illustration of this character.

FIG. 1 depicts my Red Maple tree 'RT4' in its summer habit. As shown in the Fig., my tree is shown with other Red Maple trees in the same planting, and has a similar habit and canopy to these other trees. However, the bark of my Red Maple tree is a striking reddish-brown and distinctly stands out from the gray bark of the other trees shown in the photograph. The photograph was taken in the Summer, 2004, when the tree was approximately 4 years old, approximately 3" in caliper. 18' tall, and with a 6' wide canopy.

Figure 7:
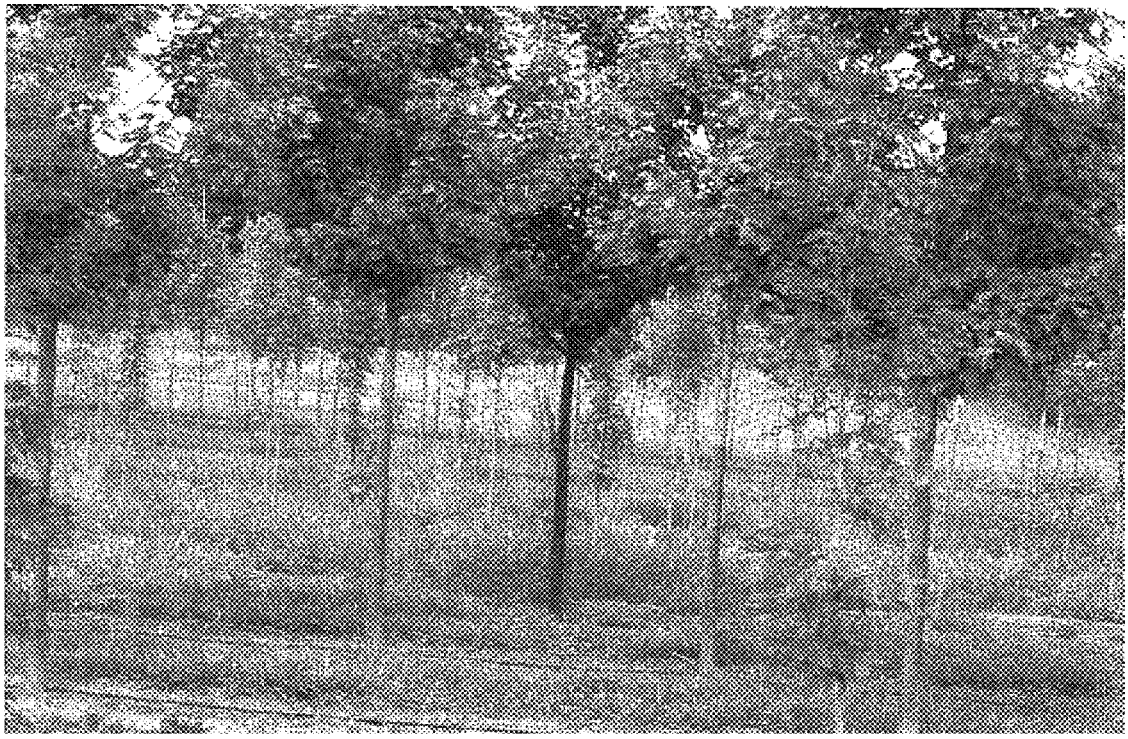

FIG. 7 is another photograph of my Red Maple tree 'RT4' in its summer habit. In the photograph, which is taken from a different angle than the photograph of FIG. 1, my tree is again shown with other Red Maple trees in the same planting, and has a similar habit and canopy to these other trees. However, the bark of my Red Maple tree is a striking reddish-brown and distinctly stands out from the gray bark of the other trees shown in the photograph. The photograph of FIG. 7 was also taken in the Summer, 2004.

DETAILED DESCRIPTION OF INVENTION

The following is a detailed description of my new variety of Red Maple tree with color terminology in accordance with The Royal Horticulture Society (R.H.S.) colour chart, except where the context indicates a term having its ordinary dictionary meaning. My new Red Maple tree has not been observed under all growing conditions, and variations may occur as a result of different growing conditions. All the progeny of my new variety, insofar as has been observed, have been identical in all of the characteristics described below.

Other than as set out below, as of this time, no other characteristics have been observed which are different from common Red Maple trees which have been observed by the inventor.

*Parentage.*—Seedling of unknown parentage grown from a bare-root liner purchased in February, 2000, from an Oregon nursery.

*Locality where grown and observed.*—Production field for a commercial nursery in Morgan County, Ga.

*Leaves.*—Typical of the species; i.e., opposite, simple, palmate, with 3 to 5 triangular ovate lobes, subcordate, acute, irregularly toothed sinuses, 2"–5" wide by 2"–4" long; dark green above like RHS green 131A, grayish green beneath like RHS green 133C; fall color typical of many cultivar and seedling red maples being primarily RHS red 43A with variations depending on growing and weather conditions; petiole green to red with variations depending on exposure to sun and plant vigor.

*Buds.*—Typical of the species; imbricate, 1/16" to 1/8", blunt, red to green, with several rounded bud scales; spherical flower buds.

*Flowers.*—Typical of the species; my new Red Maple tree has not been observed to flower, but flowering characteristics are assumed to be typical of the species; monoecious, predominantly staminate or pistillate so a single tree may produce copious amounts of fruit, or none at all. Flowers are red or sometimes yellowish in color, borne with red strap-like petals, usually opening in March and April in dense clusters before the leaves emerge. Stigmas, styles, and petals are all showy but diminutive. Each flower is attached to a red pedicel that lengthens as the flower and fruit develop. Single flowers are almost inconspicuous, measuring 1/8"–1/4" in length and width.

*Fruit.*—Assumed to be typical of the species; samara, greenish red to reddish, maturing to brown. The fruit hangs on slender pedicels 2"–3" long with wings 3/4"–1" inch long by 1/4"–1/2" wide, spreading at a narrow angle to about a 60° angle, and maturing in May to June.

Figure 1:
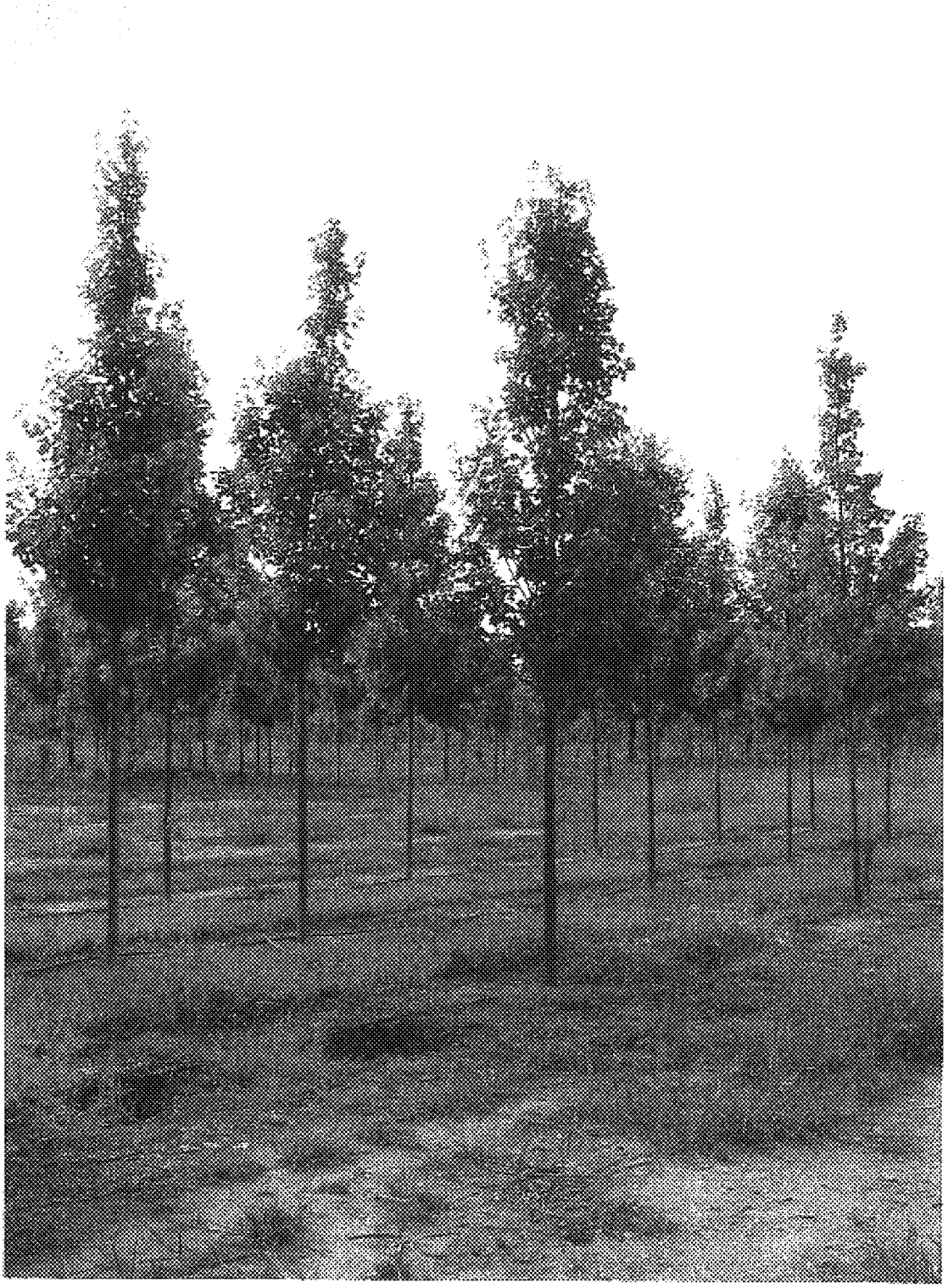
Figure 2:
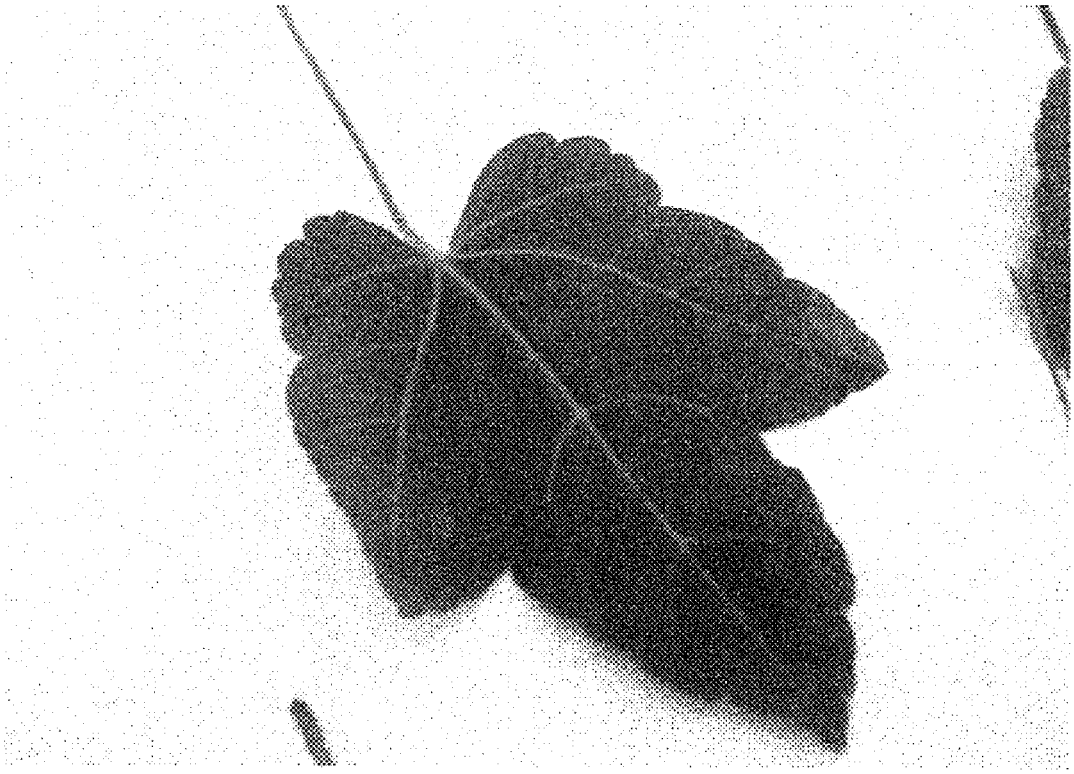
FIG. 2 is a close-up photograph of an upper leaf of my Red Maple tree 'RT4'.
Figure 3:
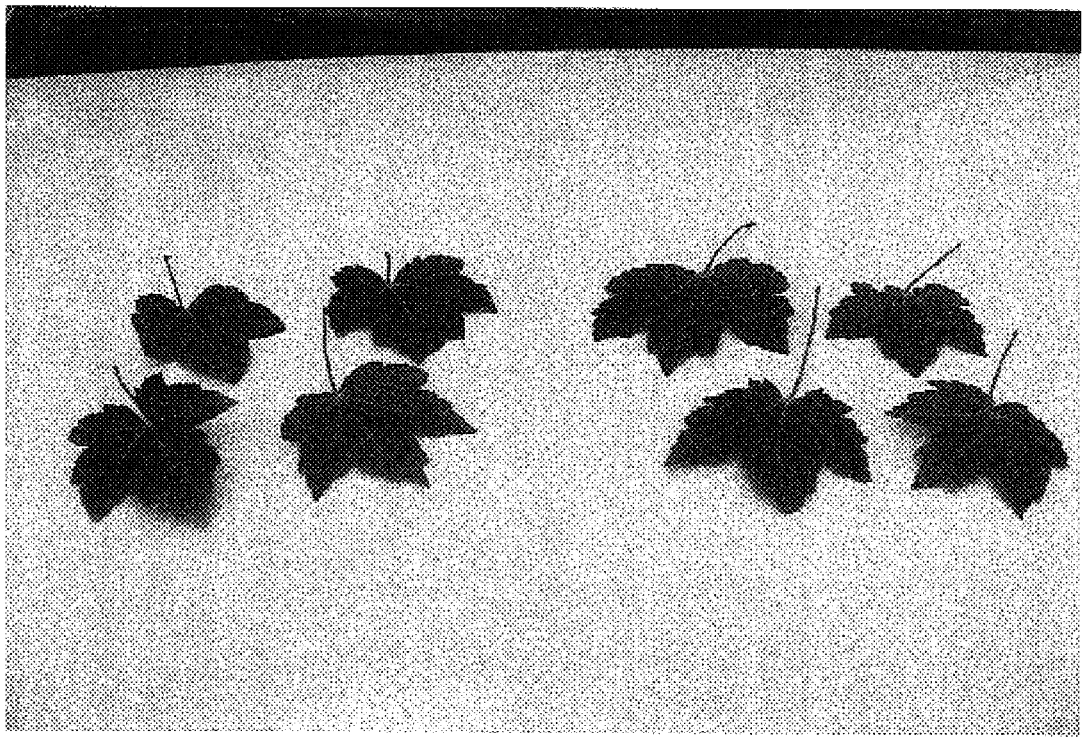
FIG. 3 is a photograph comparing upper leaves of my Red Maple tree 'RT4' with upper leaves of an October Glory® Red Maple tree.
Figure 4:
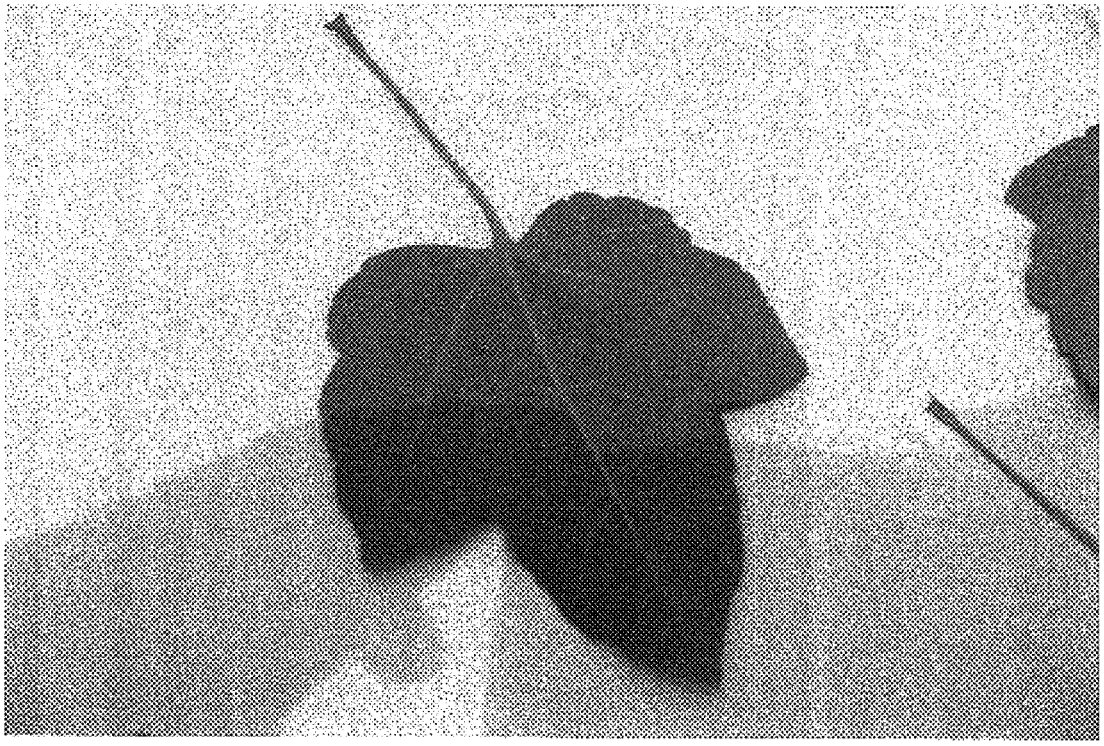
FIG. 4 is a close-up photograph of a lower leaf of my Red Maple tree 'RT4'.
Figure 5:
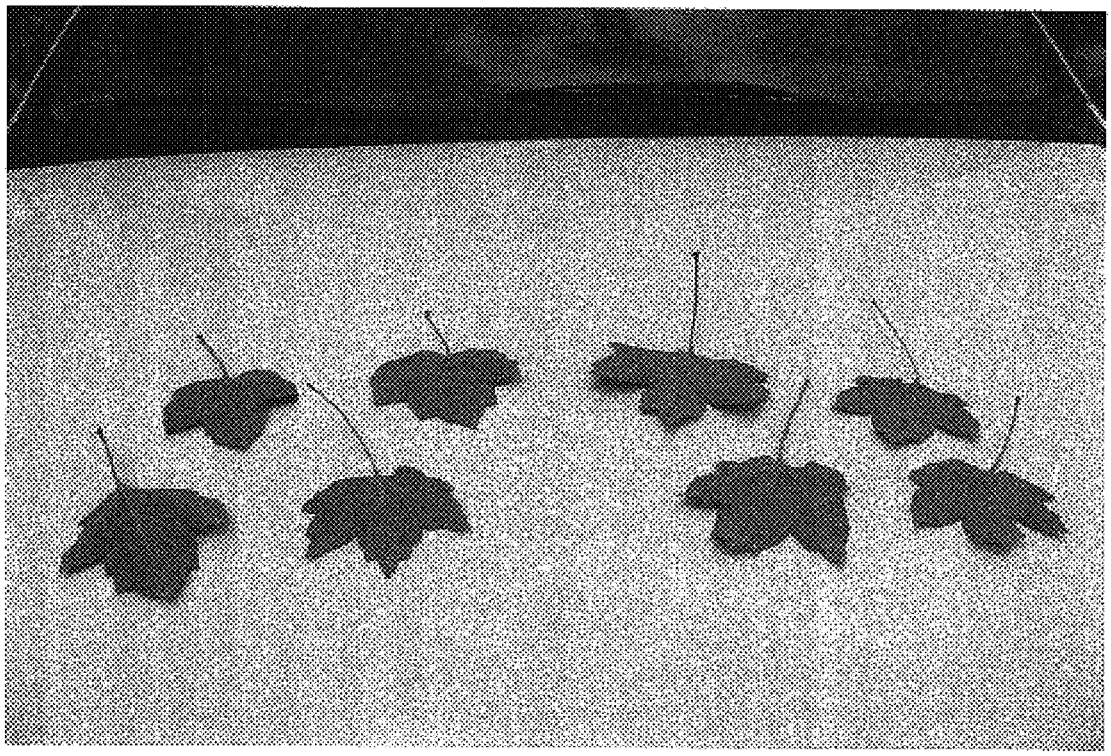
FIG. 5 is a photograph comparing lower leaves of my Red Maple tree 'RT4' with lower leaves of an October Glory® Red Maple tree.
Figure 6:
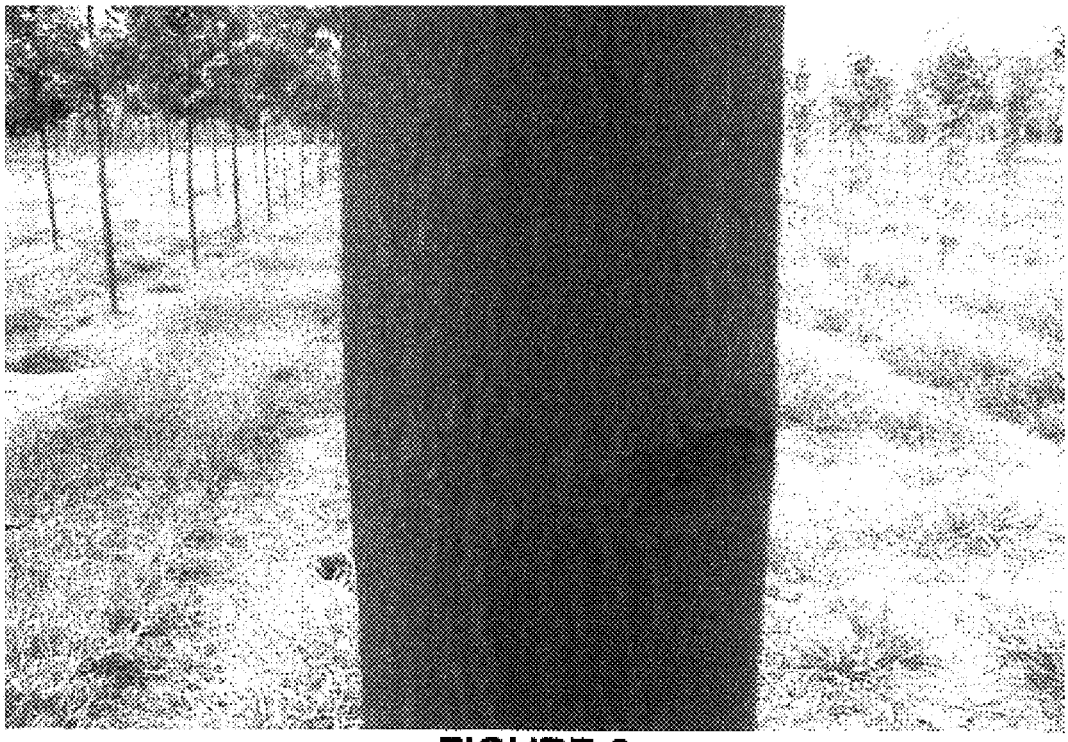
FIG. 6 is a close-up photograph of the bark of my Red Maple tree 'RT4' showing its striking reddish-brown color.

*Stem.*—Typical of the species; during the first two (2) years; glabrous, lenticelled; green-red-brown in color; becoming more reddish as winter progresses. As stems and branches mature, they become gray, as is typical of the species, and then turn a reddish-brown color like RHS grayed-orange 177A that makes my new selection unique. At a close distance, some grayish striations like RHS black 202C are visible, as shown in the photograph of FIG. 6. These striations are not visible at a distance, as shown in the photographs of FIGS. 1 and 7, and only serve to amplify the reddish-brown color present in the bark. This feature may be seen by comparing the photograph of FIG. 6 with the photographs of FIGS. 1 and 7. Branches normally assume the striking reddish-brown coloration when they reach about 1"–2" in diameter, but may develop this coloration earlier depending on growing conditions.

*Trunk.*—The trunks of Red Maple trees of the species typically have a soft gray or gray-brown color as can be seen in the photographs of FIGS. 1 and 7, and the trunks are smooth and straight as shown in these Figs. My new tree also has a smooth, straight trunk, as shown in these Figs., but has a reddish-brown bark color like RHS 177A with gray striations like RHS black 202C that is strikingly different from any other known cultivar or seedling.

*Branching.*—Typical of the species; upright, ascending branches.

*Growth habit.*—Typical of the species; moderate-fast growing, upright branching with a single leader.

*Root system.*—Typical of the species; very fibrous, transplanting well.

*Vigor.*—Typical of the species; vigorous if sited in a moist, protected area; tolerant of urban conditions but does not thrive. My new tree has been observed only in a nursery setting where it has compared favorably with other cultivar Red Maples.

*Disease.*—Various leaf spots will sporadically appear, usually in areas of low air circulation such as a production nursery where trees are grown vigorously with tight spacing; but none are significant. No foliar or other diseases have been observed on my new tree.

*Pests.*—Various pests have been observed on most all maples; leafhoppers, spider mites, tip borers, and flat-headed apple borers can all be sporadic pests in a production nursery. However, damage is usually only cosmetic and problems in the landscape are virtually unknown. Although no pests have been observed on my new tree, it is assumed that "RT4" will be susceptible to most of the pests that affect both seedling and cultivar Red Maples.

It is claimed:

1. What is claimed is a new and distinct variety of Red Maple tree named 'RT4' substantially as shown and described, and characterized particularly as to novelty by its striking reddish-brown bark.

* * * * *